United States Patent [19]

Abuto et al.

[11] Patent Number: 6,096,668

[45] Date of Patent: Aug. 1, 2000

[54] ELASTIC FILM LAMINATES

[75] Inventors: Frank Paul Abuto, Duluth; William Bela Haffner, Kennesaw; Joy Francine Jordan, Roswell; Ann Louise McCormack, Cumming, all of Ga.; Duane Girard Uitenbroek, Little Chute, Wis.

[73] Assignee: Kimberly-Clark Worldwide, Inc., Neenah, Wis.

[21] Appl. No.: 09/146,723

[22] Filed: Sep. 3, 1998

Related U.S. Application Data

[60] Provisional application No. 60/058,894, Sep. 15, 1997.

[51] Int. Cl.[7] .................................................. D04H 1/00
[52] U.S. Cl. ......................... 442/328; 442/329; 442/381; 442/394; 442/398; 428/315.9
[58] Field of Search ................................... 442/328, 329, 442/381, 394, 398; 428/315.9

[56] References Cited

U.S. PATENT DOCUMENTS

| | | | |
|---|---|---|---|
| 3,236,238 | 2/1966 | Morse | 128/290 |
| 3,454,008 | 7/1969 | Hendricks | 128/290 |
| 3,645,992 | 2/1972 | Elston | 260/80.78 |
| 4,195,634 | 4/1980 | DiSalvo et al. | 128/290 |
| 4,282,874 | 8/1981 | Mesek | 128/287 |
| 4,287,251 | 9/1981 | King et al. | 428/198 |
| 4,321,924 | 3/1982 | Ahr | 128/287 |
| 4,324,246 | 4/1982 | Mullane et al. | 128/287 |
| 4,324,247 | 4/1982 | Aziz | 128/287 |
| 4,720,415 | 1/1988 | Vander Wielen et al. | 428/152 |
| 4,726,976 | 2/1988 | Karami et al. | 428/137 |
| 4,789,699 | 12/1988 | Kieffer et al. | 524/271 |
| 4,798,603 | 1/1989 | Meyer et al. | 604/378 |
| 4,804,577 | 2/1989 | Hazelton et al. | 428/224 |
| 4,828,556 | 5/1989 | Braun et al. | 604/365 |
| 4,847,134 | 7/1989 | Fahrenkrug et al. | 428/138 |
| 4,891,258 | 1/1990 | Fahrenkrug | 428/138 |
| 4,949,668 | 8/1990 | Heindel et al. | 118/314 |
| 4,965,122 | 10/1990 | Morman | 428/225 |
| 4,983,109 | 1/1991 | Miller et al. | 425/7 |
| 5,114,781 | 5/1992 | Morman | 428/198 |
| 5,135,521 | 8/1992 | Luceri et al. | 604/383 |
| 5,171,238 | 12/1992 | Kajander | 604/383 |
| 5,188,885 | 2/1993 | Timmons et al. | 428/198 |
| 5,241,031 | 8/1993 | Mehta | 526/348.1 |
| 5,278,272 | 1/1994 | Lai et al. | 526/348.5 |
| 5,304,161 | 4/1994 | Noel et al. | 604/378 |
| 5,322,728 | 6/1994 | Davey et al. | 428/296 |
| 5,324,578 | 6/1994 | Reed et al. | 428/224 |
| 5,332,613 | 7/1994 | Taylor et al. | 428/152 |
| 5,342,334 | 8/1994 | Thompson et al. | 604/366 |
| 5,342,343 | 8/1994 | Kitaoka et al. | 604/385.2 |

(List continued on next page.)

FOREIGN PATENT DOCUMENTS

| | | |
|---|---|---|
| 0 212 284 | 3/1987 | European Pat. Off. . |
| 0 416 620 | 3/1991 | European Pat. Off. . |
| 0 586 937 | 3/1994 | European Pat. Off. . |
| 0691203 | 1/1996 | European Pat. Off. . |
| 0 712 892 | 5/1996 | European Pat. Off. . |

(List continued on next page.)

OTHER PUBLICATIONS

"New LLDPEs Offer Combined Properties, Processing Edge", Plastics World Apr. 1997, p. 8.

"Don't Say 'Metallocene,' Say 'Single–Site'", by Jan H. Schut, Plastics World, Apr. 1997, pp. 27–32.

"Here's the Latest Score on Single Site Catalysts", by Jan H. Schut, Plastics World, Apr. 1997, pp. 41–46.

*Primary Examiner*—Elizabeth M. Cole
*Attorney, Agent, or Firm*—Douglas H. Tulley, Jr.

[57] ABSTRACT

An elastic liquid impermeable laminate is disclosed having an extensible barrier film; an 8 g/m² to 100 g/m² elastomeric nonwoven web comprising fibers of low density polyethylene having a density less than 0.89 g/cm³; and an extensible cloth-like outer layer, such as a nonwoven web of spunbonded fibers. The barrier laminate can be laminated by thermal point bonding to create patterns having improved loft, excellent hand and while achieving peel strengths in excess of 500 grams.

20 Claims, 3 Drawing Sheets

U.S. PATENT DOCUMENTS

| | | | |
|---|---|---|---|
| 5,366,451 | 11/1994 | Levesque | 604/378 |
| 5,368,910 | 11/1994 | Langdon | 428/137 |
| 5,382,400 | 1/1995 | Pike et al. | 264/168 |
| 5,383,870 | 1/1995 | Takai et al. | 604/378 |
| 5,385,775 | 1/1995 | Wright | 428/284 |
| 5,387,208 | 2/1995 | Ashton et al. | 604/378 |
| 5,425,725 | 6/1995 | Tanzer et al. | 604/368 |
| 5,429,629 | 7/1995 | Latimer et al. | 604/378 |
| 5,451,450 | 9/1995 | Erderly et al. | 428/220 |
| 5,472,775 | 12/1995 | Obijeski et al. | 428/220 |
| 5,486,167 | 1/1996 | Dragoo et al. | 604/384 |
| 5,505,719 | 4/1996 | Cohen et al. | 604/372 |
| 5,520,980 | 5/1996 | Morgan et al. | 428/246 |
| 5,539,124 | 7/1996 | Etherton et al. | 548/402 |
| 5,540,976 | 7/1996 | Shawver et al. | 428/198 |
| 5,543,206 | 8/1996 | Austin et al. | 428/198 |
| 5,556,392 | 9/1996 | Koczab | 604/378 |
| 5,582,903 | 12/1996 | Levy et al. | 428/219 |
| 5,601,542 | 2/1997 | Melius et al. | 604/368 |
| 5,603,707 | 2/1997 | Trombetta et al. | 604/383 |
| 5,624,991 | 4/1997 | Harada et al. | 524/451 |
| 5,643,239 | 7/1997 | Bodford et al. | 604/370 |
| 5,651,778 | 7/1997 | Melius et al. | 604/385 |
| 5,665,083 | 9/1997 | Igaue | 604/370 |
| 5,667,864 | 9/1997 | Landoll | 428/74 |
| 5,674,341 | 10/1997 | Ng | 156/234 |
| 5,695,849 | 12/1997 | Shawver et al. | 428/131 |
| 5,714,107 | 2/1998 | Levy et al. | 264/289.3 |
| 5,728,219 | 3/1998 | Allen et al. | 118/315 |
| 5,763,333 | 6/1998 | Suzuki et al. | 442/351 |
| 5,847,053 | 12/1998 | Chum et al. | 525/240 |

FOREIGN PATENT DOCUMENTS

| | | |
|---|---|---|
| 0227481 | 7/1997 | European Pat. Off. . |
| 90/03464 | 4/1990 | WIPO . |
| 94/28224 | 12/1994 | WIPO . |
| 95/04182 | 2/1995 | WIPO . |
| 95/26878 | 10/1995 | WIPO . |
| 95/27005 | 10/1995 | WIPO . |
| 96/19346 | 6/1996 | WIPO . |
| 97/26297 | 7/1997 | WIPO . |
| 97/30843 | 8/1997 | WIPO . |

ELASTIC FILM LAMINATES

This application claims benefit of provisional application Ser. No. 60/058,894 filed Sep. 15, 1997.

FIELD OF THE INVENTION

The present invention relates to film laminates. More particularly, the present invention relates to elastic laminates of films and nonwoven fabrics.

BACKGROUND OF THE INVENTION

Film laminates have become an important article of commerce, finding a wide variety of applications including use as outer covers for personal care articles such as diapers, training pants, incontinence garments, feminine hygiene products and the like. In addition, film laminates have found use in outdoor fabrics, tarpaulins, protective apparel, infection control products, garments and the like. The films can provide the desired barrier properties to the article while other materials laminated thereto can provide additional characteristics such as strength, abrasion resistance and/or good hand.

Many articles incorporating film laminates are desirably at least partially elastic. For example, an outer cover of a diaper that is elastic will have improved body conformance relative to inelastic articles. However, achieving the desired elasticity while maintaining other desired characteristics such as breathability, good aesthetics and low cost is problematic. Low cost film laminates, such as those used in disposable articles, often suffer from poor peel strengths. Delamination of the film laminate is undesirable as it gives the appearance of an article of lesser quality and can often increase the risk of creating a rip or tear in the film.

Thus, there exists a need for a film laminate which exhibits elasticity yet which retains desired characteristics such as breathability, good hand and excellent peel strength. In addition, there exists a need for such a laminate having well defined bond patterns, loft and overall improved aesthetics. Moreover, there exists a need for such a barrier laminate which has a cloth-like outer surface, is durable and further which may employ a variety of film and laminate structures. Further, there exists a need for such a film laminate that may be fabricated by a robust process which is functional under a wide latitude of processing conditions and parameters.

SUMMARY OF THE INVENTION

The aforesaid needs are fulfilled and the problems experienced by those skilled in the art overcome by an elastic laminate of the present invention comprising an extensible base film, an elastic intermediate nonwoven web and an extensible outer fibrous material bonded thereto. The first side of the elastomeric intermediate web is bonded to the base film and the second side is bonded to the outer fibrous material. In a further aspect, the elastomeric intermediate web comprises an amorphous polymer. As an example the amorphous polymer can comprise a low density ethylene elastomer component which comprises a copolymer of ethylene and an alpha-olefin. In a further aspect, the low density polyethylene elastomer desirably has a density between about 0.86 g/cm$^3$ and about 0.89 g/cm$^3$. In addition, the amorphous polymer can comprise a blend having a second polyolefin polymer, such as a second ethylene polymer having a higher density. Desirably the low density polyethylene elastomer comprises at least about 50 weight % of the fiber. The elastic intermediate web desirably comprises a nonwoven web such as a web of meltblown fibers.

The extensible base film can comprise an elastic film and desirably comprises a breathable film. In one aspect of the present invention, the film may comprise an elastic breathable barrier such as, for example, a stretched filled-film comprising an elastomeric polyethylene polymer and a filler. The base film, elastic intermediate web and outer fibrous material preferably have a collective basis weight less than about 100 g/m$^2$. The outer fibrous material layer can comprise a thermoplastic nonwoven fabric. Desirably the outer nonwoven layer comprises a cloth-like fabric, having excellent hand and drape. In one aspect of the invention, the outer nonwoven layer comprises a necked or reversibly necked nonwoven web. The laminate of the present invention desirably has a peel strength in excess of 200 g/cm$^2$ and even more desirably in excess of 500 g/cm$^2$. Further, the breathable barrier laminate can have a WVTR in excess of 300 g/m$^2$/day, 800 g/m$^2$/day and even 1500 g/m$^2$/day. The outer fibrous material can comprise a nonwoven web and, in a further aspect can be laminated to the bonding layer by laminating the respective layers together. Suitable methods for laminating the layers includes, but is not limited to, thermal point bonding, ultrasonic bonding and the like.

DEFINITIONS

As used herein the term "nonwoven" fabric or web means a web having a structure of individual fibers or threads which are interlaid, but not in an identifiable manner as in a meshed or knitted fabric. Nonwoven fabrics or webs have been formed by many processes such as, for example, meltblowing processes, spunbonding processes, hydroentangling, air-laid and bonded carded web processes.

As used herein "microfiber web" means a web comprising fibers having an average fiber diameter less than about 10$\mu$ in at least one dimension.

As used herein the term "spunbond fibers" refers to small diameter fibers of substantially molecularly oriented polymeric material. Spunbond fibers may be formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,542,615 to Dobo et al, and U.S. Pat. No. 5,382,400 to Pike et al. Spunbond fibers are generally not tacky when they are deposited onto a collecting surface and are generally continuous. Spunbond fibers are often about 10 microns or greater in diameter. However, microfiber spunbond may be achieved by various methods including, but not limited to, those described in commonly assigned U.S. patent application Ser. Nos. 08/756,426 filed Nov. 26, 1996 to Marmon et al. and application Ser. No. 08/565,261 filed Nov. 30, 1995 to Pike et al., the contents of which are incorporated herein by reference.

As used herein the term "meltblown fibers" means fibers of polymeric material which are generally formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter. Thereafter, the meltblown fibers can be carried by the high velocity gas stream and are deposited on a collecting surface to form a web of randomly dispersed meltblown fibers. Such a process is disclosed, for example, in U.S. Pat. No. 3,849,241 to Butin et al. and U.S. Pat. No. 5,271,883 to Timmons et al. Meltblown fibers may be continuous or discontinuous and are generally tacky when deposited onto a collecting surface. Meltblown fibers can include microfiber webs.

As used herein "SMS laminate" means a spunbond/meltblown/spunbond (SMS) laminate. Examples of multi-layer nonwoven laminates are disclosed in U.S. Pat. No. 4,041,203 to Brock et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate such as by thermal point bonding as described below. Alternatively, the fabric layers may be made individually, collected in rolls, and combined in a separate bonding step.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" includes all possible spacial configurations of the molecule. These configurations include, but are not limited to isotactic, syndiotactic and random symmetries.

As used herein the term "amorphous polymer", when used herein to describe a bonding layer either as an intermediate layer or a separately applied layer, means a thermoplastic polymer such as certain polyolefins with a density in the range of from about 0.85 to about 0.89 g/cm$^3$ and low crystallinity, for example, less than about 30.

As used herein, the term "machine direction" or MD means the length of a fabric in the direction in which it is produced. The term "cross machine direction" or CD means the width of fabric, i.e. a direction generally perpendicular to the MD.

As used herein, "ultrasonic bonding" means a process performed, for example, by passing the fabric between a sonic horn and anvil roll as illustrated in U.S. Pat. No. 4,374,888 to Bornslaeger or in U.S. Pat. No. 5,591,278 to Goodman et al.

As used herein "point bonding" means bonding one or more fabrics at a plurality of discrete points. For example, thermal point bonding generally involves passing one or more layers to be bonded between heated rolls such as, for example an engraved pattern roll and a smooth calender roll. The engraved roll is, patterned in some way so that the entire fabric is not bonded over its entire surface, and the anvil roll is usually flat. As a result, various patterns for engraved rolls have been developed for functional as well as aesthetic reasons. One example of a pattern has points and is the Hansen Pennings or "H&P" pattern with about a 30% bond area when new and with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5% when new. Another typical point bonding pattern is the expanded Hansen Pennings or "EHP" bond pattern which produces a 15% bond area when new with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15% when new. Yet another common pattern is the C-Star pattern which has, when new, a bond area of about 16.9%. The C-Star pattern has a cross-directional bar or "corduroy" design interrupted by shooting stars. Other common patterns include a diamond pattern with repeating and slightly offset diamonds with about a 16% bond area and a wire weave pattern looking as the name suggests, e.g. like a window screen, with about a 15% bond area. A further pattern is the "s-weave" pattern having about a 17% bond area when new. Typically, the percent bonding area varies from around 10% to around 30% of the area of the fabric laminate web.

As used herein, the term "barrier" means a film, laminate or other fabric which is substantially impermeable to the transmission of liquids and which has a hydrohead of at least 50 mbar water. Hydrohead as used herein refers to a measure of the liquid barrier properties of a fabric. However, it should be noted that barrier fabrics of the present invention can have a hydrohead value greater than 80 mbar, 150 mbar or even 300 mbar water.

As used herein, the term "breathable" refers to a material which is permeable to water vapor having a minimum WVTR of about 300 g/m$^2$/24 hours. The WVTR of a fabric is water vapor transmission rate which, in one aspect, gives an indication of how comfortable a fabric would be to wear. WVTR (water vapor transmission rate) is measured as indicated below and the results are reported in grams/square meter/day. However, often applications of breathable barriers desirably have higher WVTRs and breathable laminates of the present invention can have WVTRs exceeding about 800 g/m$^2$/day, 1500 g/m$^2$/day, or even exceeding 3000 g/m$^2$/day.

As used herein the term "extensible" means elongatable or stretchable in at least one direction.

As used herein "elastic" means a material which, upon application of a biasing force, is stretchable, that is extensible, to a stretched, biased length which is at least 150% of its relaxed unbiased length, and which will retract at least 50 percent of its elongation upon release of the elongating force. A hypothetical example would be a one (1) inch sample of a material which is elongatable to at least 1.50 inches and which, upon release of the biasing force, will retract to a length of not more than 1.25 inches.

As used herein, the term "inelastic" or "nonelastic" refers to any material which does not fall within the definition of "elastic" above.

As used herein the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc.

As used herein the term "multicomponent fibers" refers to fibers which have been formed from at least two polymers extruded from separate extruders but spun together to form one fiber. Multicomponent fibers are also sometimes referred to as conjugate or bicomponent fibers. The polymers of a multicomponent fiber are arranged in substantially constantly positioned distinct zones across the cross-section of the fiber and extend continuously along the length of the fiber. The configuration of such a fiber may be, for example, a sheath/core arrangement wherein one polymer is surrounded by another or may be a side by side arrangement, a pie arrangement or an "islands-in-the-sea" type arrangement. Multicomponent fibers are taught in U.S. Pat. No. 5,108,820 to Kaneko et al., U.S. Pat. No. 4,795,668 to Krueger et al. and U.S. Pat. No. 5,336,552 to Strack et al. Conjugate fibers are also taught in U.S. Pat. No. 5,382,400 to Pike et al. and may be used to produce crimp in the fibers by using the differential crystallization rates of the two (or more) polymers. For bicomponent fibers, the polymers may be present in ratios of 75/25, 50/50, 25/75 or any other desired ratios. The fibers may also have shapes such as those described in U.S. Pat. No. 5,277,976 to Hogle et al., U.S. Pat. Nos. 5,466,410 to Hills and 5,069,970 and 5,057,368 to Largman et al., which describe fibers with unconventional shapes.

As used herein the term "blend" means a mixture of two or more polymers while the term "alloy" means a sub-class of blends wherein the components are immiscible but have been compatibilized.

As used herein the term "biconstituent fibers" or "multi-constituent" refers to fibers which have been formed from at least two polymers extruded from the same extruder as a blend. The term "blend" is defined above. Biconstituent fibers do not have the various polymer components arranged in relatively constantly positioned distinct zones across the cross-sectional area of the fiber and the various polymers are usually not continuous along the entire length of the fiber; instead they usually form fibrils or protofibrils which start and end at random. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

As used herein, the term "bonding window" means the range of temperature of the mechanism, e.g. a pair of heated bonding rolls, used to bond the nonwoven fabric together, over which such bonding is successful.

As used herein, the term "scrim" means a lightweight fabric used as a backing material. Scrims are often used as the base fabric for coated or laminated products.

As used herein, the term "garment" means any type of apparel which may be worn. This includes industrial work wear and coveralls, undergarments, pants, shirts, jackets, gloves, socks, and the like.

As used herein, the term "infection control product" means medically oriented items such as surgical gowns and drapes, face masks, head coverings like bouffant caps, surgical caps and hoods, footwear like shoe coverings, boot covers and slippers, wound dressings, bandages, sterilization wraps, wipers, garments like lab coats, coveralls, aprons and jackets, patient bedding, stretcher and bassinet sheets, and the like.

As used herein, the term "personal care product" means diapers, training pants, absorbent underpants, adult incontinence products, and feminine hygiene products.

As used herein, the term "protective cover" means a cover for vehicles such as cars, trucks, boats, airplanes, motorcycles, bicycles, golf carts, etc., covers for equipment often left outdoors like grills, yard and garden equipment (mowers, roto-tillers, etc.) and lawn furniture, as well as floor coverings, table cloths and picnic area covers.

DETAILED DESCRIPTION OF THE INVENTION

Figure 1:
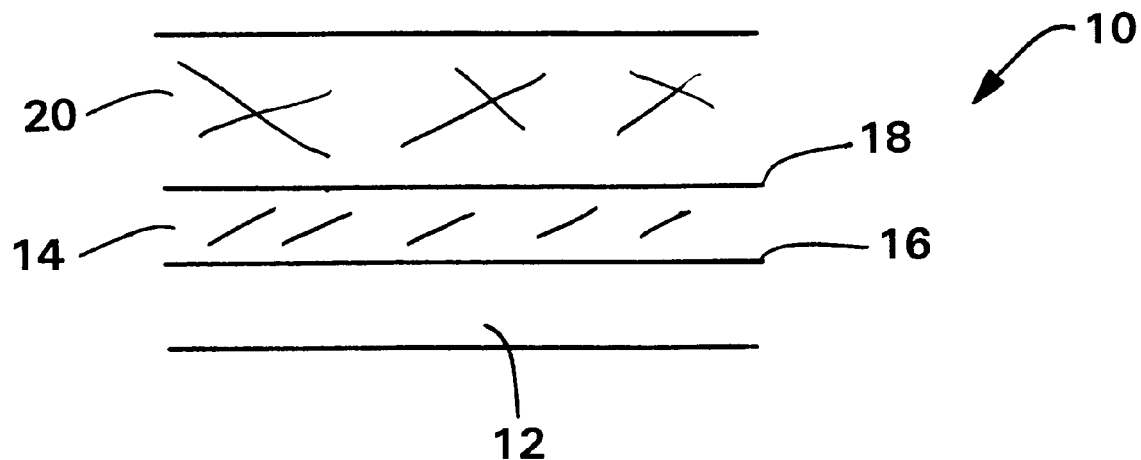
FIG. 1 is a cross-sectional view of a laminate of the present invention.

In reference to FIG. 1, the present invention is directed to a multilayer laminate 10 comprising a film 12, an outer fibrous layer 20 and an intermediate elastic nonwoven web. The intermediate nonwoven web 14 has a first side 16 and a second side 18. The outer fibrous layer 20 is attached to the second side 18 of intermediate elastic fiber nonwoven web 14 and the film 12 is attached to the first side 16 of the intermediate elastic nonwoven web 14.

The intermediate elastic nonwoven web comprises a layer of amorphous polymer fibers. The polymer composition desirably comprises an elastomer and may further include a tackifier or other bonding aid to improve adhesion between the intermediate nonwoven web and the opposed film and outer nonwoven layer(s). Examples of suitable polymers include, but are not limited to, elastomeric polyolefins, ethylene-vinyl acetate (EVA), EPDM rubbers, ethylene-ethyl acrylate (EEA), ethylene acrylic acid (EAA), ethylene methyl acrylate (EMA), polyurethane (PU), polyamide polyether block copolymers, block copolymers having the general formula A-B-A' or A-B like copoly(styrene/ ethylene-butylene), styrene-poly(ethylene-propylene)- styrene, styrenepoly(ethylene-butylene)-styrene, and the like.

In a preferred embodiment, the amorphous polymer comprises one or more elastic polyolefins such as a low density polyethylene elastomer, elastic polypropylene, flexible polyolefins, and tackified polymers such as styrenic block copolymers, polyurethanes or block polyamide polyethers. In one aspect of the present invention the intermediate elastic nonwoven web comprises, at least in part, a low density elastomeric polyolefin polymer component such as, for example, a low density ethylene elastomer component having a density less than 0.89 g/cm$^3$. Desirably the ethylene elastomer comprises a substantially linear ethylene which has a density less than 0.89 g/cm$^3$, desirably from about 0.86 g/cm$^3$ to about 0.88 g/cm$^3$ and even more desirably about 0.87 g/cm$^3$. The ethylene elastomer preferably comprises at least about 50% by weight of the polymeric portion of the fibers, and more desirable from about 70% to about 100% by weight. Preferably the ethylene elastomer comprises a polymer wherein the ethylene monomers are polymerized with an alpha-olefin such that the resulting polymer composition has a narrow molecular weight distribution ($\overline{M}_w/\overline{M}_n$), homogeneous branching and controlled long chain branching. Suitable alpha-olefins include, but are not limited to, 1-octene, 1-butene, 1-hexene and 4-methyl-pentene. Exemplary polymers include those which are known in the art as "metallocene", "constrained geometry" or "single-site" catalyzed polymers such as those described in U.S. Pat. No. 5,472,775 to Obijeski et al.; U.S. Pat. No. 5,451,450 to Erderly et al.; U.S. Pat. No. 5,539,124 to Etherton et al.; and U.S. Pat. No. 5,554,775 to Krishnamurti et al.; the entire contents of which are incorporated herein by reference.

The metallocene process generally uses a metallocene catalyst which is activated, i.e. ionized, by a co-catalyst.

Examples of metallocene catalysts include bis(n-butylcyclopentadienyl)titanium dichloride, bis(n-butylcyclopentadienyl)zirconium dichloride, bis (cyclopentadienyl)scandium chloride, bis(indenyl) zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl (cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, among others. A more exhaustive list of such compounds is included in U.S. Pat. No. 5,374,696 to Rosen et al. and assigned to the Dow Chemical Company. Such compounds are also discussed in U.S. Pat. No. 5,064,802 to Stevens et al. and also assigned to Dow. However, numerous other metallocene catalysts, single site catalysts, constrained geometry catalysts and/or comparable catalyst systems are known in the art; see for example, *The Encyclopedia of Chemical Technology*, Kirk-Othemer, Fourth Edition, vol. 17, Olefinic Polymers, pp. 765–767 (John Wiley & Sons 1996); the contents of which are incorporated herein by reference.

Regarding elastomeric polymers, U.S. Pat. No. 5,204,429 to Kaminsky et al. describes a process which may produce elastic copolymers from cycloolefins and linear olefins using a catalyst which is a stereorigid chiral metallocene transition metal compound and an aluminoxane. U.S. Pat. Nos. 5,278, 272 and 5,272,236, both to Lai et al., assigned to Dow Chemical and entitled "Elastic Substantially Linear Olefin Polymers" describe polymers having particular elastic properties, the entire contents of which are incorporated herein by reference. Suitable low density ethylene elastomers are commercially available from Dow Chemical Company of Midland, Mich. under the trade name AFFINITY, including AFFINITY EG8200 (5 MI), XU 58200.02 (30 MI), XU 58300.00 (10 MI) and from Exxon Chemical Co. of Houston, Tex. under the trade name EXACT 4049 (4.5 MI, 0.873 g/cm$^3$); 4011 (2.2 MI, 0.888 g/cm$^3$); 4041 (3 MI, 0.878 g/cm$^3$); 4006 (10 MI, 0.88 g/cm$^3$).

In addition, it is believed that the intermediate elastomeric fibrous layer may comprise a polymer blend of the amorphous polymer with one or more other polymers which comprise up to about 75% by weight of the fiber and more desirably up to about 50% of the fiber. It is believed that the fibers may comprise a low density polyethylene elastomer and additional thermoplastic polymers, desirably higher density and/or more crystalline polyolefins. Polyolefins that may be suitable for use with the present invention include, but are not limited to, LLDPE (density between about 0.90 g/cm$^3$–0.92 g/cm$^3$), LDPE (0.915–0.925 g/cm$^3$, ethylene-propylene copolymers, ethylene vinyl acetate, ethylene ethyl acrylate, ethylene acrylic acid, ethylene methyl acrylate and the like.

Examples of additional commercially available elastic polymers include, but are not limited to, Himont CATAL-LOY KS350, KS357 and KS359. Himont Catalloy polymer is an olefinic multistep reactor product wherein an amorphous ethylene propylene random copolymer is molecularly dispersed in a predominantly semicrystalline high propylene monomer/low ethylene monomer continuous matrix, such as described in U.S. Pat. No. 5,300,365 to Ogale. In addition, useful elastomeric resins include block copolymers having the general formula A-B-A' or A-B, where A and A' are each a thermoplastic polymer endblock which contains a styrenic moiety such as a poly (vinyl arene) and where B is an elastomeric polymer midblock such as a conjugated diene or a lower alkene polymer. Block copolymers of the A-B-A' type can have different or the same thermoplastic block polymers for the A and A' blocks, and the present block copolymers are intended to embrace linear, branched and radial block copolymers. In this regard, the radial block copolymers may be designated $(A-B)_m-X$, wherein X is a polyfunctional atom or molecule and in which each $(A-B)_m$-radiates from X in a way that A is an endblock. In the radial block copolymer, X may be an organic or inorganic polyfunctional atom or molecule and m is an integer having the same value as the functional group originally present in X. It is usually at least 3, and is frequently 4 or 5, but not limited thereto. Thus, in the present invention, the expression "block copolymer", and particularly "A-B-A'" and "A-B" block copolymer, is intended to embrace all block copolymers having such rubbery blocks and thermoplastic blocks as discussed above, which can be extruded (e.g., by meltblowing), and without limitation as to the number of blocks. The elastomeric nonwoven web may be formed from, for example, elastomeric (polystyrene/poly (ethylenebutylene)/polystyrene) block copolymers. Commercial examples of such elastomeric copolymers are, for example, those known as KRATON materials which are available from Shell Chemical Company of Houston, Tex. KRATON block copolymers are available in several different formulations, a number of which are identified in U.S. Pat. Nos. 4,663,220 and 5,304,599, the entire contents of which are hereby incorporated by reference.

Polymers composed of an elastomeric A-B-A-B tetrablock copolymer may also be used in the practice of this invention. Such polymers are discussed in U.S. Pat. No. 5,332,613 to Taylor et al. In such polymers, A is a thermoplastic polymer block and B is an isoprene monomer unit hydrogenated to substantially a poly(ethylene-propylene) monomer unit. An example of such a tetrablock copolymer is a styrene-poly(ethylenepropylene)-styrene-poly(ethylene-propylene) or SEPSEP elastomeric block copolymer available from the Shell Chemical Company of Houston, Tex. under the trade designation KRATON.

Other exemplary elastomeric materials which are believed suitable for use with the present invention include polyurethane elastomeric materials such as, for example, those available under the trademark ESTANE from B. F. Goodrich & Co. or MORTHANE from Morton Thiokol Corp., polyester elastomeric materials such as, for example, those available under the trade designation HYTREL from E. I. DuPont De Nemours & Company, and those known as ARNITEL formerly available from Akzo Plastics of Arnhem, Holland and now available from DSM of Sittard, Holland.

In order to improve the thermal compatibility of the intermediate nonwoven web with those of the adjoining layers, it may be desirable to add a tackifier or bonding aid to the elastic polymer composition. Examples of suitable tackifiers include, but are not limited to those described in U.S. Pat. No. 4,789,699 to Kieffer et al. Examples of commercially available tackifiers are REGALREZ 1126 available from Hercules Inc. of Wilmington, Del.; ESCOREZ 5300 from Exxon Chemical Co. and WING-TACK 95 from Goodyear Chemical Co. of Akron, Ohio. The amount of tackifier added will vary with respect to the particular elastic polymer employed in the intermediate elastic fiber layer and those polymers comprising adjoining layers. Although the amount of tackifier added to the elastic intermediate layer will vary, often addition of about 5 to about 20% by weight of the polymer composition is desirable.

In a preferred embodiment, the intermediate elastic nonwoven web comprises a matrix of fibers, such as a web of meltblown fibers. In a further aspect the fibrous elastic layer may comprise a layer of spunbond fibers and/or staple length fibers of similar basis weight, desirably the nonwoven web has a basis weight of between about 10 g/m$^2$ and about 100 g/m$^2$, and more desirably a basis weight between about 25 g/m$^2$ and about 60 g/m$^2$. The selection of the basis weight will vary with respect to the basis weight of the overall laminate as well as the recovery properties of the film and/or outer nonwoven layer. Where both the outer nonwoven layer and film are extensible but inelastic materials, a higher basis weight intermediate elastic fiber layer will often be required to provide an overall laminate with elastic properties. However, where the film and/or outer nonwoven layer is also elastic, the intermediate elastic web can comprise less of the overall laminate basis weight.

The extensible film may comprise either a mono-layer or multi-layer film. In addition, non-porous and microporous films are believed suitable for use with the present invention. Desirably the film comprises a barrier layer and also exhibits good drape; such films desirably have a basis weight between about 15 g/m$^2$ and 100 g/m$^2$ and, even more desirably, between about 20 g/m$^2$ and 60 g/m$^2$. Thermoplastic polymers used in the fabrication of the films of the present invention include, but are not limited to, polyolefins including homopolymers, copolymers, terpolymers and blends thereof. In addition, flexible polyolefin films are also believed suitable for use in the present invention. Additional film forming polymers which may be suitable for use with the present invention, alone or in combination with other polymers, include ethylene vinyl acetate (EVA), ethylene ethyl acrylate (EEA), ethylene acrylic acid (EAA), ethylene methyl acrylate (EMA), ethylene normal butyl acrylate (EnBA), polyurethane (PU), poly(ether-ester) and poly (amid-ether) block copolymers. However, elastomeric polyolefin polymers are preferred such as, for example, polymers of ethylene and propylene as well as copolymers, terpolymers and blends thereof; examples include, but are not limited to, elastomeric polyolefins and ethylene-propylene copolymer blends.

In one aspect of the invention, the film can comprise a breathable barrier comprising such as, for example, microporous films having a WVTR of at least 300 g/m$^2$/day, and more desirably having a WVTR in excess of 800 g/m$^2$/day or 1500 g/m$^2$/day. Breathable microporous film can be formed by any one of various methods known in the art. As an example, the breathable barrier film can comprise a stretched filled-film which includes a thermoplastic polymer and filler. These (and other) components can be mixed together, heated and then extruded into a monolayer or multilayer film. The filled film may be made by any one of a variety of film forming processes known in the art such as, for example, by using either cast or blown film equipment. The thermoplastic polymer and filler can be stretched in at least one direction, thereby reducing the film gauge or thickness and creating a network of micropores of a size and frequency to achieve the desired level of breathability. Examples of breathable barrier films suitable for use with the present invention are described in WO 95/16562 filed Jun. 22, 1995 to McCormack; WO 96/19346 filed Jun. 27, 1996 to McCormack et al.; U.S. patent application Ser. No. 08/722,726 filed Oct. 1, 1996 to McCormack et al.; U.S. patent application Ser. No. 08/883,164 filed Jun. 26, 1997 to McCormack et al.; U.S. patent application Ser. No. 08/882,712 filed Jun. 25, 1997 to McCormack et al.; U.S. patent application Ser. No. 08/843,147 filed Apr. 25, 1997 to Gwaltney et al; U.S. patent application Ser. No. 09/122,326 filed Jul. 24, 1998 and Application Express Mail No. RB879664401 US filed Sep. 15, 1997 to Shawver et al.; the entire content of the aforesaid references are incorporated herein by reference. Such films, prior to stretching, desirably have a basis weight of less than about 100 g/m$^2$ and even more desirably less than about 60 g/m$^2$. Upon stretching the multilayer film desirably has a basis weight of less than 60 g/m$^2$ and even more desirably between about 15 and 35 g/m$^2$. Suitable films can also include multilayer films such as, for example, those formed by co-extrusion; see for example the methods of forming multilayer films as disclosed in U.S. Pat. No. 4,522,203; U.S. Pat. No. 4,494,629; and U.S. Pat. No. 4,734,324 the entire contents of which are incorporated herein by reference.

The outer layer may comprise an extensible fibrous material capable of being laminated to the elastic intermediate web. The outer layer may comprise, as an example, extensible nonwoven materials, meshed fabrics, scrims, loosely woven fabrics, elastic composite materials and/or other like materials. Desirably the fabric comprises one or more layers of thermoplastic fibers which are inherently extensible or which have been treated so as to be become extensible and/or elastic and which also have a cloth-like hand and drape. Examples of suitable extensible and/or elastic materials are described in U.S. Pat. Nos. 4,965,122 to Morman et al.; 5,114,781 to Morman et al.; 5,336,545 to Morman et al.; 4,720,415 to Vander Wielen et al.; 4,789,699 to Kieffer et al.; 5,332,613 to Taylor et al.; 5,288,791 to Collier et al.; U.S. Pat. No. 4,663,220 to Wisneski et al.; 5,540,976 to Shawver et al.; European Application No. 0,712,892 A1 to Djiaw et al.; U.S. application Ser. No. 08/603,961 to Shawver et al. and U.S. application Ser. No. 08/674,365 to Levy et al., the entire contents of which are incorporated herein by reference. The composition of the thermoplastic polymer may be selected as desired to achieve a material having the desired properties, such as elasticity, hand, tensile strength, cost etc. Further, the outer nonwoven layer may be treated such as, for example, by embossing, hydroentangling, mechanically softening, printing, anti-static treatment or treated in an other manner in order to achieve desired aesthetics and/or functional characteristics.

Nonwoven composite materials comprising an elastic layer bonded to a gathered nonwoven web, such as described in U.S. Pat. No. 4,729,415 to Vander Wielen et al., are well suited for use with the present invention. Such elastic composite materials can be made by (a) tensioning an elastic web (which may comprise a fibrous web such as a nonwoven web of elastomeric fibers) to elongate it; (b) bonding the elongated elastic web to at least one gatherable web (which can comprise a nonwoven web such as a spunbond fiber web) under conditions which soften at least portions of the elastic web to form a bonded composite web; and (c) relaxing the composite web immediately after the bonding step whereby the gatherable web is gathered to form the composite elastic material.

It is possible to emboss various attractive patterns within the elastic laminate of the present invention, for example, patterns suitable for outer covers of an infant diaper. Exemplary bonding and/or embossing patterns can be seen with reference to FIGS. 4 and 5. Other bonding patterns may also be utilized in connection with the present invention such as, for example, those described in U.S. patent application Ser. No. 08/754,419 filed Dec. 17, 1996. In this regard, it has been found that laminates of the present invention exhibit improved definition and loftier pattern bonding. Moreover, excellent patterns are achievable while providing a laminate with excellent drape and peel strengths. Laminates of the present invention exhibit a peel strengths in excess of 500 g and even 1000 g. In addition, while achieving such peel strength elastic laminates can be formed having a drape between about 1 and 7 cm. In one embodiment the outer layer may comprise an 8 to 35 g/m² web of necked polypropylene spunbond fibers having a pattern printed upon and/or embossed therein.

In addition, the polymers compositions comprising the fibers and/or film may optionally include one or more stabilizers, additives or other materials to achieve desired attributes. Preferably the compositions include an anti-oxidant such as, for example, a hindered phenol stabilizer. Commercially available anti-oxidants include, but are not limited to, IRGANOX E 17 (α-tocopherol) and IRGANOX 1076 (octodecyl 3,5-di-tert-butyl-4-hydroxyhydrocinnamate) which are available from Ciba Specialty Chemicals of Terrytown, N.Y. In addition, other stabilizers or additives which are compatible with the film forming process, stretching and any subsequent lamination steps may also be employed with the present invention. For example, additional additives may be added to impart desired characteristics to the film such as, for example, melt stabilizers, processing stabilizers, heat stabilizers, light stabilizers, heat aging stabilizers and other additives known to those skilled in the art. Generally, phosphite stabilizers (i.e. IRGAFOS 168 available from Ciba Specialty Chemicals of Terrytown, N.Y and DOVERPHOS available from Dover Chemical Corp. of Dover, Ohio) are good melt stabilizers whereas hindered amine stabilizers (i.e. CHIMASSORB 944 and 119 available from Ciba Specialty Chemicals of Terrytown, N.Y.) are good heat and light stabilizers. Stabilizer packages comprising mixtures of one or more of the above stabilizers are also commercially available such as, for example, B900 available from Ciba Specialty Chemicals.

Figure 2:
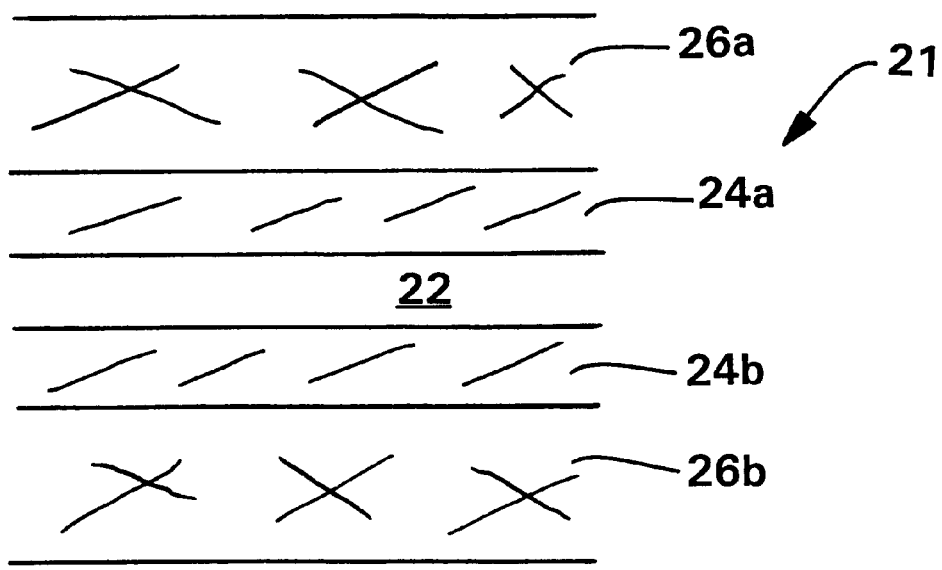
FIG. 2 is a cross-sectional view of a laminate of the present invention.

In a further aspect of the invention and in reference to FIG. 2, the breathable barrier laminate 21 may comprise a barrier film 22 with opposed elastic meltblown fiber layers 24a and 24b each bonded to a side of the film 22. Outer nonwoven layers 26a and 26b are bonded to the elastic meltblown fiber layers 24a and 24b; for example the layers can be point bonded. The opposed layers 22a and 22b as well as opposed layers 26a and 26b can comprise either the same or different materials.

Figure 3:
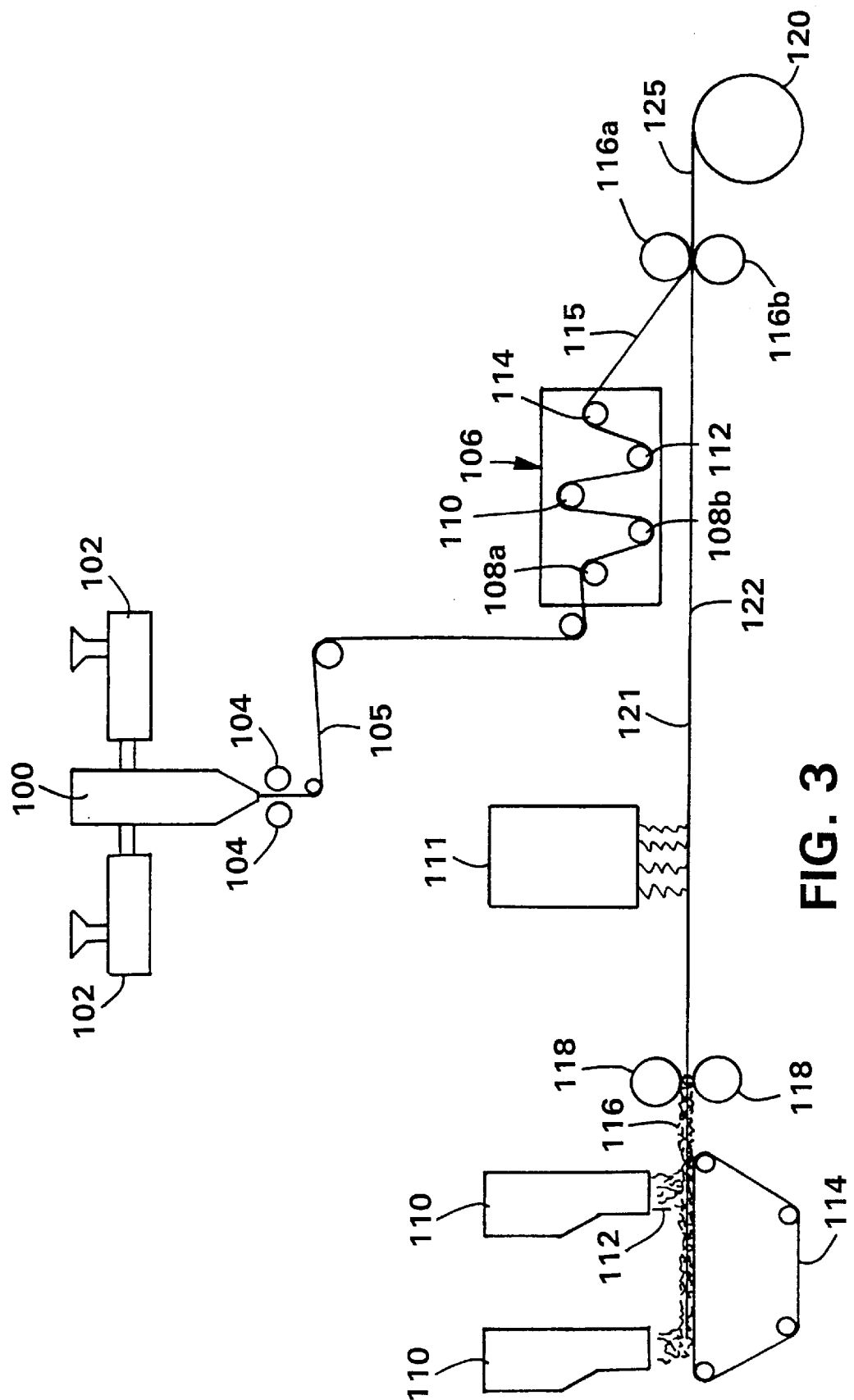
FIG. 3 is a schematic diagram of a process line for making a laminate of the present invention.

In reference to FIG. 3, a schematic diagram of a process line for fabricating a barrier laminate of the present invention. Referring to FIG. 3, the film 105 can be formed from an extrusion film apparatus 100 such as a cast or blown unit as was previously described above. Typically the apparatus 100 will include one or more polymer extruders 102. The unstretched film 105 is extruded into a pair of nip or chill rollers 104 one of which may be patterned so as to impart an embossed pattern to the newly formed film 105. The basis weight of the unstretched film is desirably between about 50 g/m² and about 100 g/m². However, it will be appreciated by those skilled in the art that the basis weight of the unstretched film will be based on the desired basis weight of the stretched film, the stretch ratio and other factors. As indicated above, filler may be added to the film extrudate in order to achieve a breathable film upon stretching.

From the extrusion film apparatus 100 the unstretched film 105 is directed to a film stretching unit 106 such as a machine direction orienter which is a commercially available device from vendors such as the Marshall and Williams Company of Providence, R.I. Such an apparatus 106 has a plurality of preheat and stretching rollers which stretch and thin the unstretched film 105 in the machine direction of the film which is the direction of travel of the film 105 through the process. The film can be stretched in either a single or multiple discrete stretching operations. With regard to FIG. 3, heated rollers 108a and 108b may act as pre-heat rolls. Slow roll 110 is also heated and travels at a circumferential speed slower than that of fast roll 112. The different speeds of the adjacent rollers act to stretch the film 105. After stretching the film 115 may be allowed to slightly retract and/or be further heated or annealed by one or more heated rollers, such as by heated anneal roll 114. After exiting the film stretching unit 106 the stretched film 115 desirably has a maximum basis weight of approximately 50 g/m², and even more desirably having a basis weight between about 15 to about 35 g/m².

Figure 5:
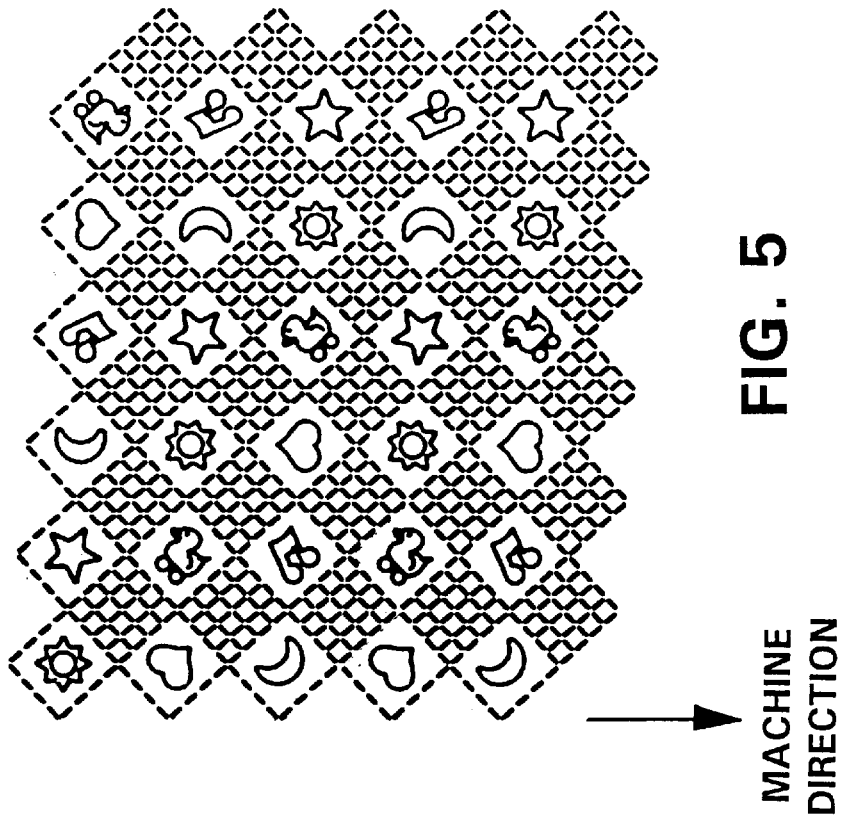
FIG. 5 is a view of a bonding pattern suitable for use with the present invention.
Figure 4:
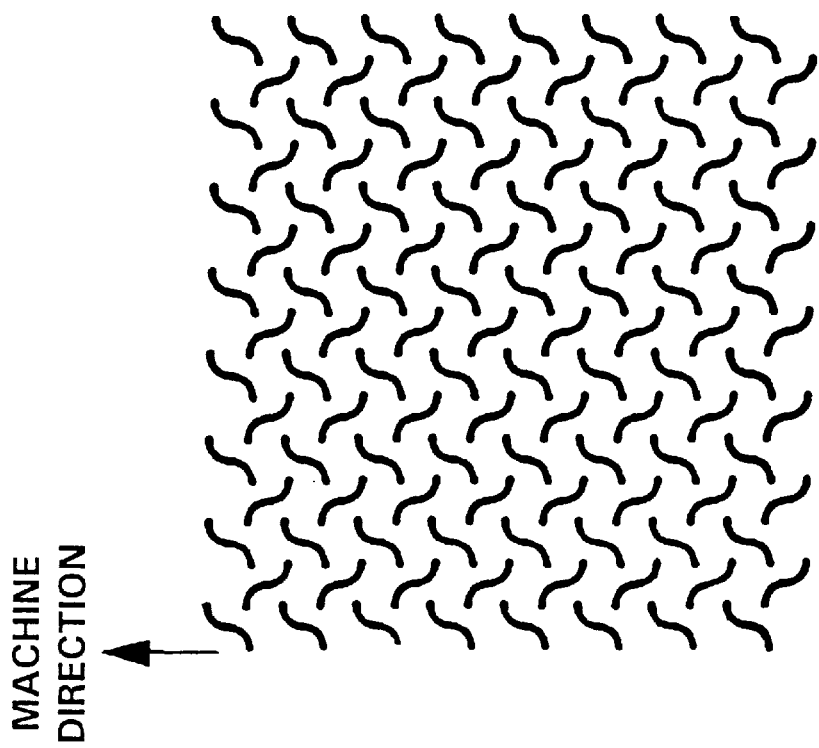
FIG. 4 is a view of a bonding pattern suitable for use with the present invention.

The stretched film 115 is attached to the elastomeric amorphous polymer fiber web and one or more outer nonwoven layers 22 to form a film/nonwoven laminate 125. Still referring to FIG. 3, conventional nonwoven web forming apparatus 111, such as meltblown machines and second conventional nonwoven web forming apparatus 110, such as a spunbond machines, can be used to form the elastomeric meltblown layer 121 and overlying outer nonwoven layers 122. The long, essentially continuous spunbond fibers 112 are deposited onto a forming wire 114 as an unbonded web 116 and may then sent through a pair of compaction and/or bonding rolls 118 to add sufficient integrity to the web for further processing. The spunbond fibers may be through-air bonded or point bonded, such as with an s-weave pattern as shown in FIG. 4. Once the film 115 has been thinned as desired and the elastomeric amorphous polymer fiber web 121 and outer layer 122 have been formed, the layers can be brought together and laminated to one another using a pair of bonding or laminating rolls 116. The bonding rolls 116 are desirably heated and at least one of the rolls may be patterned to create a desired bond pattern with a prescribed bond surface area for the resultant laminate 125. The maximum bond point surface area of the laminate 126 generally does not exceed about 50 percent of the total surface area, desirably being between about 5% and about 30%. There are a number of bond patterns which may be used. As an example, a baby objects pattern is shown in FIG. 5. Once the laminate 125 exits the bonding or laminating roll 116, it may be wound up into a winder roll 120. Alternatively, the laminate 125 may continue in-line for further processing and/or conversion.

The barrier laminates of the present invention may be used to make and/or comprise a component of protective covers, infection control products, personal care products, garments and other articles that desirably have barrier properties and conformability. As examples thereof, the barrier laminates may be used as back sheet or an outer cover in a diaper or adult incontinence garments or in a surgical gown.

TESTS

Hydrohead: A measure of the liquid barrier properties of a fabric is the hydrohead test. The hydrohead test determines the height of water or amount of water pressure (in millibars) that the fabric will support before liquid passes therethrough. A fabric with a higher hydrohead reading indicates it has a greater barrier to liquid penetration than a fabric with a lower hydrohead. The hydrohead can be performed according to Federal Test Standard 191A, Method 5514. The hydrohead data cited herein was obtained using a test similar to the aforesaid Federal Test Standard except modified as indicated below. The hydrohead was determined using a hydrostatic head tester available from Marlo Enterprises, Inc. of Concord, N.C. The specimen is subjected to a standardized water pressure (as opposed to using an actual column of water), increased at a constant rate until leakage appears on the surface of the fabric in three separate areas. (Leakage at the edge, adjacent clamps is ignored.) Unsupported fabrics, such as a thin film, can be supported to prevent premature rupture of the specimen.

Melt Index: The melt index is a measure of the viscosity of a polymer under a given set of conditions. The MI is expressed as the weight of material which flows from a capillary of known dimensions under a specified load or shear rate for a measured period of time and is measured in grams/10 minutes at 190° C. and load of 2160 g according to ASTM test 1238-90b.

WVTR: The water vapor transmission rate (WVTR) for the sample materials was calculated in accordance with ASTM Standard E96-80. Circular samples measuring three inches in diameter were cut from each of the test materials and a control which was a piece of CELGARD 2500 film from Hoechst Celanese Corporation of Sommerville, N.J. CELGARD 2500 film is a microporous polypropylene film. Three samples were prepared for each material. The test dish was a number 60-1 Vapometer pan distributed by Thwing-Albert Instrument Company of Philadelphia, Pa. One hundred milliliters of water were poured into each Vapometer pan and individual samples of the test materials and control material were placed across the open tops of the individual pans. Screw-on flanges were tightened to form a seal along the edges of the pan, leaving the associated test material or control material exposed to the ambient atmosphere over a 6.5 centimeter diameter circle having an exposed area of approximately 33.17 square centimeters. The pans were placed in a forced air oven at 100° F. (37° C.) or 1 hour to equilibrate. The oven was a constant temperature oven with external air circulating through it to prevent water vapor accumulation inside. A suitable forced air oven is, for example, a Blue M Power-O-Matic 60 oven distributed by Blue M. Electric Company of Blue Island, Ill. Upon completion of the equilibration, the pans were removed from the oven, weighed an immediately returned to the oven. After 24 hours, the pans were removed from the oven and weighed again. The preliminary test water vapor transmission rate values were calculated with Equation (I) below:

Test WVTR=(grams weight loss over 24 hours)×315.5 $g/m^2/24$ hours  (I)

The relative humidity within the oven was not specifically controlled.

Under the predetermined set conditions of 100° F. (37° C.) and ambient relative humidity, the WVTR for the CELGARD 2500 control has been defined to be 5000 grams per square meter for 24 hours. Accordingly, the control sample was run with each test and the preliminary test values were corrected to set conditions using Equation (II) below:

WVTR=(Test WVTR/control WVTR)×(5000 $g/m^2/24$ hours)  (II)

Peel test: In peel or delamination testing a laminate is tested for the amount of tensile force which will pull the layers of the laminate apart. Values for peel strength are obtained using a specified width of fabric, clamp jaw width and a constant rate of extension. For samples having a film side, the film side of the specimen is covered with masking tape or some other suitable material in order to prevent the film from ripping apart during the test. The masking tape is on only one side of the laminate and so does not contribute to the peel strength of the sample. This test uses two clamps, each having two jaws with each jaw having a facing in contact with the sample, to hold the material in the same plane, usually vertically, separated by 2 inches to start. The sample size is 4 inches wide by as much length as necessary to delaminate enough sample length. The jaw facing size is 1 inch high by at least 4 inches wide, and the constant rate of extension is 300 mm/min. The sample is delaminated by hand a sufficient amount to allow it to be clamped into position and the clamps move apart at the specified rate of extension to pull the laminate apart. The sample specimen is pulled apart at 180° of separation between the two layers and the peel strength reported as an average of peak load in grams. Measurement of the force is begun when 16 mm of the laminate has been pulled apart and continues until a total of 170 mm has been delaminated. The Sintech 2 tester, available from the Sintech Corporation, 1001 Sheldon Dr., Cary, N.C. 27513, the Instron Model TM, available from the Instron Corporation, 2500 Washington St., Canton, Mass. 02021, or the Thwing-Albert Model INTELLECT II available from the Thwing-Albert Instrument Co., 10960 Dutton Rd., Phila., Pa. 19154, may be used for this test. Results are reported as an average of three specimens and may be performed with the specimen in the cross direction (CD) or the machine direction (MD).

Drape: The drape stiffness test determines the bending length of a fabric using the principle of cantilever bending of the fabric under its own weight. A higher number indicates a stiffer fabric. The bending length is a measure of the interaction between fabric weight and fabric stiffness. A 1 inch (2.54 cm) by 8 inch (20.3 cm) fabric strip is slid, at 4.75 inches per minute (12 cm/min) in a direction parallel to its long dimension so that its leading edge projects from the edge of a horizontal surface. The length of the overhang is measured when the tip of the specimen is depressed under its own weight to the point where the line joining the tip of the fabric to the edge of the platform makes a 41.5 degree angle with the horizontal. The drape stiffness is calculated as 0.5×bending length. A total of 5 samples of each fabric should be taken. This procedure conforms to ASTM standard test D-1388 except for the fabric length which is different (longer). The test equipment used is a Cantilever Bending tester model 79-10 available from Testing Machines Inc., 400 Bayview Ave., Amityville, N.Y. 11701. As in most testing, the sample should be conditioned to ASTM conditions of 65±2 percent relative humidity and 72±2° F. (22±1° C.), or TAPPI conditions of 50±2 percent relative humidity and 72±1.8 ° F. prior to testing.

EXAMPLE 1

A film was extruded in a conventional film casting process from a compound having the following composition (percentages by weight): 47% Supercoat calcium carbonate (1 micron average particle size, available from English China Clay of America, Sylacauga, Ala.), 53% AFFINITY PL-1280 resin (an ethylene-1-octene copolymer, 0.90 $g/cm^3$ density, 5 MI, available from Dow Plastics, Freeport, Tex.), 2000 ppm of B900 stabilizer blend (available from Ciba-Geigy Corp., Terrytown, N.Y.). The extruded film was approximately 1.5 mils thick. This film was then stretched to make it breathable using a machine-direction-orientor (MDO), such equipment which is available, for example, from the Marshall and Williams Company. The preheat and stretching rolls were at 160° F., annealing rolls at room temperature and at 180° F., film inlet speed at 50 (feet per minute) (fpm) and outlet speed at 200 fpm to give a 4X stretch ratio (an elongation of 300% of the original film length). The oriented film was then thermally laminated in-line to a necked spunbond on which a meltblown layer was previously applied. The bonder temperature controllers were set to 180° F. on the anvil (smooth steel roll) and 250° F. for the C-star pattern roll. The spunbond used was 17 g/m² wire weave pattern bonded propylene homopolymer, necked 45% and overlaid with 17 g/m² meltblown fiber web comprising a low density polyethylene elastomer available from Dow under the designation ENGAGE 52800.02 resin (30 MI, 0.870 g/cm³ density). In the bonder nip the film was contacting the anvil roll, the meltblown was between the film and the spunbond, and the spunbond contacted the patterned roll. The resulting laminate had an attractive, well-defined pattern. Peel strength was measured at 384.5 g MD and 308.2 CD, and the WVTR was 790 g/m²/24 hours. The laminate also exhibited desirable elastic behavior: when extended in the CD to 150% of its starting length, in the first extension cycle the force to stretch it to 130% was 657 g/3 inch width, and the retraction force in the second cycle at 130% elongation was 130 g/3 inch width.

EXAMPLE 2

A three layer elastic barrier laminate was made comprising an elastic film layer, a fibrous elastomeric meltblown bonding layer, and a CD extensible nonwoven outer layer. The elastic film 12 was a 1.0 mil non-porous film type XMAX264.0 from Consolidated Thermoplastics Company of Chippewa Falls, Wis. The elastomeric intermediate layer was a 30 g/m² meltblown web made from polyethylene elastomer, AFFINITY 58200.02. The resin had a melt index of 30 and a density of 0.87 grams/cm³. The nonwoven, CD extensible support layer comprised a 36% neckstretched, side by side polypropylene/polyethylene bicomponent spunbond with a basis weight of 33.9 g/m². The polypropylene was ESCORENE PD 3445 obtained from Exxon Chemical Company of Houston, Tex. and the polyethylene was Dow 6831. The three layers were thermally point bonded using an EHP bond pattern at a temperature of 135° F. (57° C.) and a nip pressure of about 30 psi (206.9 kPa) at a speed less than 3 meters/min. A 76.2 MD by 152.4 mm CD width section of the laminate was elongated to a length of 304.8 mm. Upon the release of the biasing force, the laminate returned to a final length of 109.5 mm. The laminate had an CD/MD peel strength of about 2000 grams and drape values in the range of 2 to 4 cm.

While the invention has been described in detail with respect to specific embodiments thereof, it will be apparent to those skilled in the art that various alterations, modifications and other changes may be made to the invention without departing from the spirit and scope of the present invention. It is therefore intended that the claims cover all such modifications, alterations and other changes encompassed by the appended claims.

We claim:

1. A film laminate comprising:
   an extensible polymeric barrier film;
   an extensible thermoplastic polymer nonwoven outer layer; and
   an elastic intermediate nonwoven web of fibers comprising an amorphous polyethylene polymer having a density between about 0.85 g/cm³ and 0.89 g/cm³ and wherein said elastic intermediate nonwoven web is bonded to both said barrier film and said extensible nonwoven outer layer and further wherein said laminate is elastic.

2. The film laminate of claim 1 wherein said elastic fibrous web comprises an elastic meltblown fiber web having a basis weight between about 8 g/m² and 100 g/m² and wherein said film laminate has a peel strength in excess of 200 g.

3. The film laminate of claim 2 where said extensible nonwoven outer layer comprises a necked nonwoven fabric.

4. The film laminate of claim 2 wherein said extensible nonwoven outer layer comprises a reversibly necked nonwoven fabric.

5. The film laminate of claim 2 wherein the polymer comprising said extensible polymeric barrier film is an elastic polymer and said film is elastic.

6. The film laminate of claim 2 wherein said extensible nonwoven outer layer comprises an elastic nonwoven web.

7. The film laminate of claim 4 wherein said elastic meltblown fiber web has a basis weight less than about 34 g/m².

8. The film laminate of claim 1 wherein said elastic intermediate nonwoven web comprises a polyethylene elastomer having a density between about 0.86 g/cm³ and about 0.89 g/m³.

9. The film laminate of claim 2 wherein said elastic intermediate nonwoven web comprises a blend of a polyethylene elastomer having a density between about 0.86 g/cm³ and 0.89 g/cm' and a second polyethylene having a density above 0.90 g/cm³.

10. The film laminate of claim 8 wherein said extensible nonwoven outer layer comprises a necked nonwoven fabric and said extensible polymeric barrier film comprises an elastic filled film having a WVTR greater than 300 g/m²/hours.

11. The film laminate of claim 1 wherein said barrier film has a WVTR in excess of 800 g/m²/24 hours.

12. The film laminate of claim 11 wherein said elastic intermediate nonwoven web comprises a meltblown fiber web.

13. The film laminate of claim 12 wherein said intermediate nonwoven web has a basis weight less than about 34 g/m².

14. The film laminate of claim 12 wherein said barrier film comprises a microporous film.

15. The film laminate of claim 14 wherein said barrier film comprises a polyolefin polymer, said extensible outer nonwoven layer comprises a polyolefin polymer and wherein said film laminate has a peel strength in excess of 500 g.

16. The film laminate of claim 15 wherein said barrier film comprises a polyethylene polymer and filler and further wherein voids are located adjacent said filler.

17. The film laminate of claim 15 wherein said barrier film comprises a polypropylene polymer and filler and further wherein voids are located adjacent said filler.

18. The film laminate of claim 15 wherein said elastic intermediate nonwoven web comprises a polyethylene elastomer having a density between about 0.86 g/cm³ and about 0.89 g/cm³.

19. The film laminate of claim 15 wherein said elastic intermediate nonwoven web comprises a blend of a polyethylene elastomer having a density between about 0.86 g/cm³ and 0.89 g/cm³ and a second polyethylene having a density above 0.90 g/cm³.

20. The film laminate of claim 14 wherein said nonwoven outer layer comprises an elastic nonwoven composite material having an elastic web bonded to a gathered nonwoven web.

* * * * *